United States Patent
Kaminski et al.

(10) Patent No.: US 11,660,281 B2
(45) Date of Patent: May 30, 2023

(54) COMPOSITIONS AND METHODS OF TREATING OR PREVENTING FIBROTIC LUNG DISEASES

(71) Applicant: YALE UNIVERSITY, New Haven, CT (US)

(72) Inventors: Naftali Kaminski, New Haven, CT (US); Guoying Yu, Orange, CT (US); Argyrios Tzouvelekis, Athens (GR)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/624,485

(22) PCT Filed: Jun. 26, 2018

(86) PCT No.: PCT/US2018/039530
§ 371 (c)(1),
(2) Date: Dec. 19, 2019

(87) PCT Pub. No.: WO2019/005816
PCT Pub. Date: Jan. 3, 2019

(65) Prior Publication Data
US 2020/0113863 A1 Apr. 16, 2020

Related U.S. Application Data

(60) Provisional application No. 62/526,817, filed on Jun. 29, 2017.

(51) Int. Cl.
*A61K 31/222* (2006.01)
*A61K 31/4412* (2006.01)
*A61K 31/496* (2006.01)
*A61P 11/00* (2006.01)

(52) U.S. Cl.
CPC ........ *A61K 31/222* (2013.01); *A61K 31/4412* (2013.01); *A61K 31/496* (2013.01); *A61P 11/00* (2018.01)

(58) Field of Classification Search
CPC ............... A61K 31/192; A61K 31/196; A61K 31/4418; A61K 31/496; A61K 31/222; A61K 31/4412; A61K 31/662; A61K 9/0075; A61K 9/0078; A61K 9/008; A61K 8/008; A61P 11/00
See application file for complete search history.

(56) References Cited

U.S. PATENT DOCUMENTS

| | | | |
|---|---|---|---|
| 4,997,644 A | 3/1991 | Hunter | |
| 5,883,294 A * | 3/1999 | Scanlan | C07C 59/84 562/471 |
| 9,498,536 B2 | 11/2016 | Mousa et al. | |
| 2011/0044981 A1 | 2/2011 | Spangler et al. | |
| 2014/0017329 A1 | 1/2014 | Mousa et al. | |
| 2017/0105956 A1 | 4/2017 | Kaminski et al. | |
| 2017/0119776 A1 | 5/2017 | Beck et al. | |

FOREIGN PATENT DOCUMENTS

| | | |
|---|---|---|
| CN | 107469086 A | 12/2017 |
| EP | 3634426 A1 | 4/2020 |
| WO | 2009089093 A1 | 7/2009 |
| WO | 2014178892 A1 | 11/2014 |
| WO | 2015191841 A1 | 12/2015 |
| WO | 2018226604 A1 | 12/2018 |
| WO | 2019178023 A1 | 9/2019 |

OTHER PUBLICATIONS

Extended European Search Report for European Patent Application No. 18823876.0 dated Mar. 5, 2021.
International Search Report and Written Opinion issued for PCT International Application No. PCT/US2018/039530, dated Sep. 7, 2018.
Columbano, et al., "The thyroid hormone receptor-beta agonist GC-1 induces cell proliferation in rat liver and pancreas". Endocrinology. 147(7), 2006, 3211-3218.
Lindemann, et al., "Sobetirome: the past, present and questions about the future", Expert Opin Ther Targets. 20(2), 2016, 145-149.
"Extended European Search Report and Opinion dated Dec. 9, 2021, for European Application No. 19766664, 5 pages".
Song, Zhi-Fang, et al., "Experimental study of glucocorticoid in the treatment of acuterespiratory distress syndrome induced by *E. coli*", Chinese Critical Care Med , vol. 18(12), Nov. 30, 2006, 716-720.

* cited by examiner

*Primary Examiner* — Sarah Pihonak
(74) *Attorney, Agent, or Firm* — Saul Ewing LLP; Kathryn Doyle; Domingos J. Silva

(57) ABSTRACT

The present invention includes a method of preventing and/or treating a fibrotic lung disease in a subject. In certain embodiments, the method comprises administering to the subject a thyroid receptor β-agonist. The invention further comprises compositions useful within the invention, as well as kits comprising compositions useful within the invention.

22 Claims, 9 Drawing Sheets

COMPOSITIONS AND METHODS OF TREATING OR PREVENTING FIBROTIC LUNG DISEASES

CROSS-REFERENCE TO RELATED APPLICATION

The present application is a 35 U.S.C. § 371 national phase application of, and claims priority to, International Application No. PCT/US2018/039530, filed Jun. 26, 2018, which claims priority under 35 U.S.C. § 119(e) to U.S. Provisional Application No. 62/526,817, filed Jun. 29, 2017, the disclosures of all of which are incorporated herein by reference in their entireties.

BACKGROUND OF THE INVENTION

Pulmonary fibrosis constitutes the end stage of a broad range of heterogeneous interstitial lung diseases, characterized by deposition of extracellular matrix and extensive remodeling of the normal lung parenchyma. More than 200 causes of pulmonary fibrosis have been identified so far, including genetic disorders, autoimmune diseases, environmental exposures to toxins and chemical warfare, drugs and radiation. The most common form is idiopathic pulmonary fibrosis (IPF), which is pathologically indistinguishable from other forms.

IPF is a devastating chronic lung disease with yet unknown etiology. IPF leads to death in 3.5-4 years from initial diagnosis in more than 50% of the patients, regardless of treatment. Despite extensive research efforts to understand IPF, its pathogenesis is still elusive and controversial.

With a gradually increasing worldwide incidence and no proven therapies other than lung transplantations, IPF treatment represents a major challenge for both pharmaceutical industries and chest physicians. To date, available treatment agents have limited therapeutic efficacy, and are associated with side effects, ranging from major (such as immune suppression and subsequent infections, acute exacerbations of disease, and excessive bleeding) to minor (including gastrointestinal complications, such as diarrhea and nausea), which significantly affect the patient's quality of life. So far, none of the agents tried had any significant effect on patient survival.

Early during embryonic development, definitive embryonic progenitor cells of the developing foregut become committed to various organ domains, including the lung and thyroid. In line with the premise of common embryonic origin, lung and thyroid share several common transcriptional regulators of their development such as NK2 Homeobox 1 (Nkx2-1) and thyroid transcription factor 1 (TTF-1). In particular, Nkx2-1 knockout mice display lung and thyroid agenesis, while humans born with Nkx2-1 gene mutations develop pediatric lung disease, hypothyroidism, and neurological impairment. In addition, TTF-1, a 38KD nuclear transcription factor that belongs in the Nkx2 superfamily and is predominantly found in both normal type II alveolar epithelial cells and thyroid tissue, plays an essential role in epithelial morphogenesis, stimulating the synthesis of surfactant proteins and regulating secretory product gene transcription in Clara cells. TTF-1 is used by pathologists as a reliable histologic marker in the differential diagnosis of both thyroid tumors as well as pulmonary adenocarcinoma. Studies in murine models have shown that exogenous administration of thyroid hormones (thyroxine, also known as T4, and its potent derivative, triiodothyronine, also known as T3) accelerates surfactant production, alveolar formation, and fetal lung maturation. Unfortunately, investigational trials of thyroid replacement therapy for premature infants with respiratory distress syndrome (RDS) showed mixed and irreproducible results. The exact mechanisms through which thyroid hormones exert their therapeutic potentials are unknown, and these compounds have not been successfully used in the treatment of lung fibrosis.

There is a need in the art to identify therapeutic treatments that can be used to treat or prevent fibrotic lung diseases, such as IPF. The present invention addresses and meets this need.

BRIEF SUMMARY OF THE INVENTION

The invention provides a method of preventing and/or treating a fibrotic lung disease in a subject in need thereof. The invention further provides a kit that is useful within the methods of the invention.

In certain embodiments, the method comprises administering to the subject a therapeutically effective amount of at least one thyroid receptor (TR) β-agonist.

In certain embodiments, the TR β-agonist comprises at least one selected from the group consisting of GC-1 (2-(4-(4-hydroxy-3-isopropylbenzyl)-3,5-dimethylphenoxy) acetic acid), KB-2115 (3-[3,5-dibromo-4-(4-hydroxy-3-propan-2-ylphenoxy)anilino]-3-oxopropanoic acid), KB-141 ((\{3,5-dichloro-4-[4-hydroxy-3-(propan-2-yl)phenoxy]phenyl\} acetic acid), MB07811 ((4S)-4-(3-chlorophenyl)-2-[(3,5-dimethyl-4-(4-hydroxy-3-isopropylbenzyl)phenoxy)methyl]-2-oxido-[1,3,2]-dioxaphosphonane), and MB07344 (3,5-dimethyl-4-(4'-hydroxy-3'-isopropylbenzyl)phenoxy methylphosphonic acid), or any salt, ester, or solvate thereof. In other embodiments, the TR β-agonist comprises GC-1, or any salt, ester, or solvate thereof.

In certain embodiments, the fibrotic lung disease comprises idiopathic pulmonary fibrosis.

In certain embodiments, the TR β-agonist is the only pharmaceutically active agent administered to the subject. In other embodiments, the TR β-agonist is the only pharmaceutically active agent administered to the subject in sufficient amount to treat or prevent the fibrotic lung disease.

In certain embodiments, the subject is further administered at least one additional agent that treats, prevents, or reduces the symptoms of the fibrotic lung disease. In other embodiments, the at least one additional agent comprises at least one selected from the group consisting of pirfenidone and nintedanib.

In certain embodiments, the subject is administered a daily dose of TR β-agonist ranging from about 10 to about 40 μg/kg.

In certain embodiments, administration of the TR β-agonist does not cause significant or undesirable cardiac stimulation, weight loss, and/or blood lipid decrease in the subject.

In certain embodiments, the TR β-agonist is administered to the subject at a frequency selected from the group consisting of about three times a day, about twice a day, about once a day, about every other day, about every third day, about every fourth day, about every fifth day, about every sixth day, and about once a week.

In certain embodiments, the TR β-agonist is administered to the subject through a route selected from the group consisting of oral, parenteral, nasal, intravenous, subcutaneous, enteral, pulmonary, aerosol, ophthalmic, inhalational, intratracheal, intrabronchial, and topical.

In certain embodiments, the subject is a mammal. In other embodiments, the mammal is a human.

In certain embodiments, the kit comprises at least one TR β-agonist, an applicator, and an instructional material for use thereof. In other embodiments, the instructional material comprises instructions for preventing or treating a fibrotic lung disease in a subject comprising administering the at least one TR β-agonist to the subject. In yet other embodiments, the kit further comprises at least one additional agent that treats, prevents, or reduces the symptoms of the fibrotic lung disease. In yet other embodiments, the at least one additional agent comprises pirfenidone or nintedanib.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 2A: Collagen deposition in mice was assessed by hydroxyproline content. Data are expressed as mean hydroxyproline content per lung set (μg/gr lung)+SEM, n=8 mice/group, *p<0.05. FIGS. 2A-2D: Quantitative RT-PCR analysis of Col1a1 (collagen, type I, alpha 1), Col3a1 (collagen, type III, alpha 1) and FSP1 (fibroblast-specific protein 1) relative expression in the bleomycin model of lung fibrosis. Bars (means±SEM) are shown for the relative changes (fold) by setting the indicated control level to 1.0, *p<0.05. FIG. 2E: Masson's Trichrome staining of representative lung sections (n=2) from each group of treated mice. A significant decrease in collagen deposition can be seen in the interstitium, peribronchiolar, or perivascular space in treated mice.

FIGS. 3A-3C: Quantitative RT-PCR analysis of Ppargc1a, Thra and Thrb relative expression in the bleomycin model of lung fibrosis. Bars (means±SEM) are shown for the relative changes (fold) by setting the indicated control level to 1.0, n=8 mice/group, *p<0.05.

FIG. 5A: Hydroxyproline level in mice was assessed. Data are expressed as mean hydroxyproline content per lung set (μg/gr lung)+SEM, n=8 mice/group, *p<0.05. FIGS. 5B-5F: Quantitative RT-PCR analysis of Col1a1 (collagen, type I, alpha 1), Col3a1 (collagen, type III, alpha 1), FSP1 (fibroblast-specific protein 1), Acta (alpha-actin-2), and Ppargc1a (peroxisome proliferator-activated receptor gamma coactivator 1-alpha) relative expression in the bleomycin model of lung fibrosis. Bars (means±SEM) are shown for the relative changes (fold) by setting the indicated control level to 1.0, *p<0.05. FIG. 5E: Masson's Trichrome staining of representative lung sections (n=2) from each group of treated mice. A significant decrease in collagen deposition can be seen in the interstitium, peribronchiolar, or perivascular space in treated mice.

DETAILED DESCRIPTION OF THE INVENTION

Figure 1:
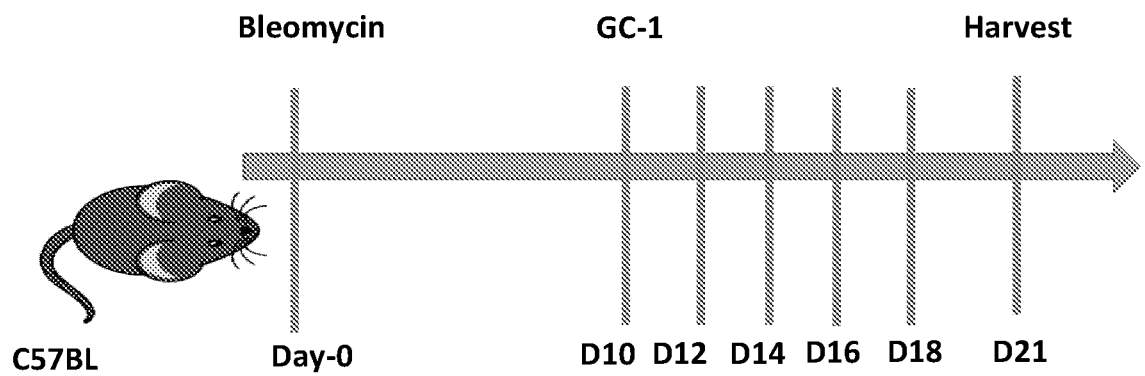
FIG. 1 illustrates a non-limiting experiment where mice with bleomycin-induced fibrosis were treated with GC-1 (also known as 2-[4-[[4-hydroxy-3-(1-methylethyl)phenyl] methyl]-3,5-dimethylphenoxy]acetic acid) intraperitoneally. On Day 0, bleomycin was delivered intratracheally to the mice (1.5 U/kg). On days 10-18, the mice were administered 30 μg/kg of GC-1 (200 μl) or equivalent volume of vehicle (normal saline 0.9%).

The present invention relates in part to the unexpected discovery that administration of a thyroid receptor (TR) beta-agonist (β-agonist) to a subject afflicted with a fibrotic lung disease results in attenuation or complete resolution of the fibrotic process in the subject. In certain embodiments, the TR β-agonist is the only pharmaceutically active agent administered to the subject. In other embodiments, the TR β-agonist is the only pharmaceutically active agent administered to the subject in sufficient amount to treat or prevent the fibrotic lung disease.

In certain embodiments, the TR β-agonist comprises at least one selected from the group consisting of GC-1 (also known as sobetirome or 2-(4-(4-hydroxy-3-isopropylbenzyl)-3,5-dimethylphenoxy)acetic acid), KB-2115 (also known as eprotirome or 3-[3,5-dibromo-4-(4-hydroxy-3-propan-2-ylphenoxy)anilino]-3-oxopropanoic acid), KB-141 (({3,5-dichloro-4-[4-hydroxy-3-(propan-2-yl)phenoxy]phenyl}acetic acid), MB07811 ((4S)-4-(3-chlorophenyl)-2-[(3,5-dimethyl-4-(4-hydroxy-3-isopropylbenzyl)phenoxy)methyl]-2-oxido-[1,3,2]-dioxaphosphonane), and MB07344 (3,5-dimethyl-4-(4'-hydroxy-3'-isopropylbenzyl) phenoxy methylphosphonic acid), or an ester, salt or solvate thereof. In other embodiments, administration of the TR β-agonist does not cause significant or undesirable cardiac stimulation, such as but not significantly or undesirably elevated heart rate, significant or undesirable blood lipid decrease, and/or significant or undesirable weight loss.

As reported herein, administration of a TR β-agonist to a bleomycin-induced fibrotic mouse blunts the disease in the animal. Significant decrease in collagen deposition was seen in the interstitium, peribronchiolar, or perivascular space in the treated mice.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, non-limiting methods and materials are described.

As used herein, each of the following terms has the meaning associated with it in this section.

Abbreviations used herein include: Acta (alpha-actin-2); Col1a1, collagen, type I, alpha 1; Col3a1, collagen, type III, alpha 1; FSP1, fibroblast-specific protein 1; GC-1, 2-[4-[[4-Hydroxy-3-(1-methylethyl)phenyl]methyl]-3,5-dimethylphenoxy]acetic acid, or an ester, salt, or solvate thereof; IPF, idiopathic pulmonary fibrosis; Nkx2-1, NK2 Homeobox 1; Ppargc1a, Peroxisome proliferator-activated receptor gamma coactivator 1-alpha; RDS, respiratory distress syndrome; T3, triiodothyronine; T4, thyroxine; Thra, thyroid hormone receptor alpha; Thrb, thyroid hormone receptor beta; TR, thyroid receptor; TTF-1, thyroid transcription factor 1; UIP, usual interstitial pneumonia.

As used herein, the articles "a" and "an" are used o refer to one or to more than one (i.e., to at least one) of the grammatical object of the article. By way of example, "an element" means one element or more than one element.

As used herein, "about," when referring to a measurable value such as an amount, a temporal duration, and the like, is meant to encompass variations of ±20% or ±10%, in certain embodiments ±5%, in certain embodiments ±1%, and in certain embodiments ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

In one aspect, the terms "co-administered" and "co-administration" as relating to a subject refer to administering to the subject a compound of the invention or salt thereof along with a compound that may also treat the disorders or diseases contemplated within the invention. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "composition" or "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound include, but are not limited to, intravenous, oral, aerosol, parenteral, ophthalmic, nasal, inhalational, intratracheal, intrapulmonary, intrabronchial, inhalation, and topical administration.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "fibrotic lung disease" or "fibroid lung disease" or "pulmonary fibrosis" or "scarring of the lung" refers to a group of diseases characterized by the formation or development of excess fibrous connective tissue (fibrosis) in the lungs. Symptoms of pulmonary fibrosis are mainly: shortness of breath, particularly with exertion; chronic dry, hacking coughing; fatigue and weakness; chest discomfort; and loss of appetite and rapid weight loss. Pulmonary fibrosis may be a secondary effect of other diseases, most of them being classified as interstitial lung diseases, such as autoimmune disorders, viral infections or other microscopic injuries to the lung. Pulmonary fibrosis can also appear without any known cause ("idiopathic"). Idiopathic pulmonary fibrosis is a diagnosis of exclusion of a characteristic set of histologic/pathologic features known as usual interstitial pneumonia (UIP).

Diseases and conditions that may cause pulmonary fibrosis as a secondary effect include: inhalation of environmental and occupational pollutants (asbestosis, silicosis and gas exposure); hypersensitivity pneumonitis, most often resulting from inhaling dust contaminated with bacterial, fungal, or animal products; cigarette smoking; connective tissue diseases such as rheumatoid arthritis, SLE; scleroderma, sarcoidosis and Wegener's granulomatosis; infections; medications such as amiodarone, bleomycin (pingyangmycin), busulfan, methotrexate, apomorphine and nitrofurantoin; and radiation therapy to the chest.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The terms "patient," "subject" or "individual" are used interchangeably herein, and refer to any animal, or cells thereof whether in vitro or in situ, amenable to the methods described herein. In a non-limiting embodiment, the patient, subject or individual is a mammal, such as for example a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions.

The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

By the term "specifically bind" or "specifically binds," as used herein, is meant that a first molecule preferentially binds to a second molecule (e.g., a particular receptor or enzyme), but does not necessarily bind only to that second molecule.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

Compounds and Compositions

In certain embodiments, thyroid receptor β-agonists are useful within the methods of the invention. Non-limiting examples of thyroid hormones contemplated within the invention include, but are not limited to, sobetirome or GC-1, eprotirome or KB-2115, KB-141, MB07811, and MB07344, or an ester (such as an optionally substituted phenyl, benzyl, $C_1$-$C_{12}$ alkyl, or $C_3$-$C_8$ cycloalkyl ester), salt or solvate thereof.

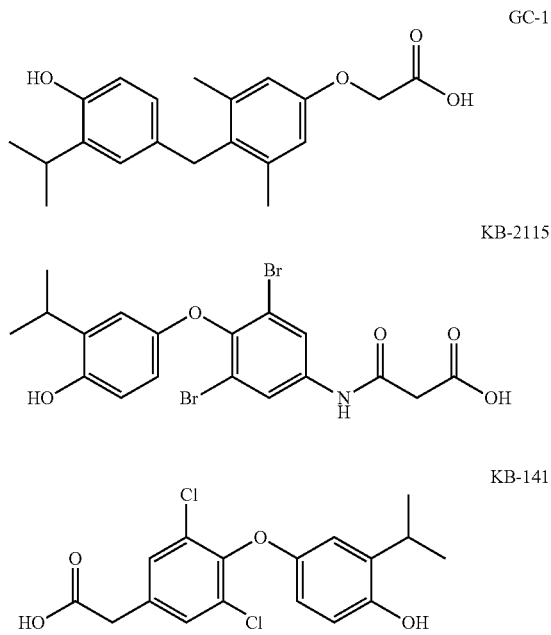

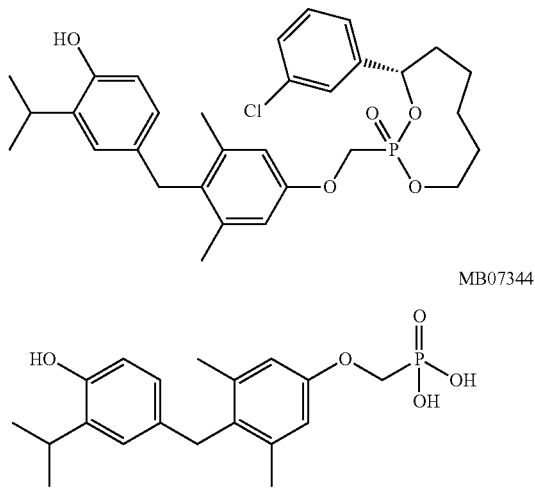

Esters contemplated within the invention include, but are not limited to, methyl, ethyl, n-propyl, isopropyl, n-butyl, sec-butyl, isobutyl, t-butyl, n-pentyl, phenyl, benzyl, cyclopropyl, cyclobutyl, cyclopentyl, cyclohexyl, and the like.

The compounds used in the methods described herein may form salts with bases, and such salts are included in the present invention. In certain other embodiments, the salts are pharmaceutically acceptable salts. The term "salts" embraces addition salts of free acids and/or bases that are useful within the methods of the invention. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable base addition salts of compounds used in the methods of the invention include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, ammonium, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate base with the compound. Salts may be comprised of a fraction of less than one, one, or more than one molar equivalent of base with respect to any compound of the invention.

In certain other embodiments, the at least one compound of the invention is in a pharmaceutical composition further including at least one pharmaceutically acceptable carrier. Certain formulations useful within methods of the invention can be found in US 2014/0017329 and WO 2009/089093, which are incorporated herein in their entireties by reference.

The methods and formulations described herein include the use of crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain other embodiments, the compounds described herein exist in solvated forms with pharmaceutically acceptable solvents such as water, and ethanol. In other embodiments, the compounds described herein exist in unsolvated form.

The compounds used in the methods of the invention may possess one or more stereocenters, and each stereocenter may exist independently in either the (R) or (S) configuration. In certain other embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain other embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In certain other embodiments, the compounds of the invention exist as tautomers. All tautomers are included within the scope of the compounds recited herein.

In certain other embodiments, compounds described herein are prepared as prodrugs. A "prodrug" is an agent converted into the parent drug in vivo. In certain other embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain other embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain other embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain other embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain other embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and in the art. General methods for the preparation of compound as described herein are modified by the use of appropriate reagents and conditions, for the introduction of the various moieties found in the formula as provided herein.

Methods

The invention includes a method of preventing and/or treating a fibrotic lung disease in a subject in need thereof. In certain embodiments, the method comprises administering to the subject therapeutically effective amounts of at least one TR β-agonist, such as but not limited to GC-1 or KB-2115.

In certain embodiments, the fibrotic lung disease comprises IPF.

In certain embodiments, the subject is administered a daily dose of TR β-agonist ranging from about 10 to about 40 µg/kg.

In certain embodiments, the compositions of the invention are administered to the subject about three times a day, about twice a day, about once a day, about every other day, about every third day, about every fourth day, about every fifth day, about every sixth day and/or about once a week. In other embodiments, the subject is further administered at least one additional bioactive agent that treats, prevents or reduces the symptoms of the fibrotic lung disease.

In certain embodiments, the subject is a mammal. In other embodiments, the mammal is a human.

Kits

The invention includes a kit comprising at least a TR β-agonist, an applicator, and an instructional material for use thereof. The instructional material included in the kit comprises instructions for preventing or treating a fibrotic lung disease contemplated within the invention in a subject. The instructional material recites the amount of, and frequency with which, the at least one TR β-agonist should be administered to the subject. In other embodiments, the kit further comprises at least one additional bioactive agent that treats, prevents or reduces the symptoms of a fibrotic lung disease.

Combination Therapies

In certain embodiments, the compounds of the invention are useful in the methods of the invention in combination with at least one additional compound useful for treating or preventing fibrotic lung disease. This additional compound may comprise compounds identified herein or compounds, e.g., commercially available compounds, known to treat, prevent or reduce the symptoms of fibrotic lung disease.

Non-limiting examples of additional compounds contemplated within the invention include pirfenidone (5-methyl-1-phenylpyridin-2-one, or a salt or solvate thereof) and nintedanib (methyl (3Z)-3-{[(4-{methyl [(4-methylpiperazin-1-yl)acetyl]amino}phenyl)amino](phenyl)methylidene}-2-oxo-2,3-dihydro-1H-indole-6-carboxylate, or a salt or solvate thereof).

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from 1 ng/kg/day and 100 mg/kg/day. One of ordinary skill in the art would be able to study the relevant factors and make the determination regarding the effective amount of the therapeutic compound without undue experimentation.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle.

In certain other embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier.

In yet other embodiments, the compound of the invention is the only biologically active agent (i.e., capable of treating or preventing diseases and disorders contemplated herein) in the composition. In yet other embodiments, the compound of the invention is the only biologically active agent (i.e., capable of treating or preventing diseases and disorders contemplated herein) in therapeutically effective amounts in the composition. In yet other embodiments, the compound of the invention is co-administered with one or more addition biologically active agents (i.e., capable of treating or preventing diseases and disorders contemplated herein).

In certain other embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, and/or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, aerosol, ophthalmic, inhalational, intratracheal, intrapulmonary, intrabronchial, and topical or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the invention include oral, nasal, pulmonary, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Pulmonary Administration

Routes of administration of any of the compositions of the invention include nasal, inhalational, intratracheal, intrapulmonary, intrabronchial, and inhalation.

Suitable compositions and dosage forms include, for example, dispersions, suspensions, solutions, syrups, granules, beads, powders, pellets, liquid sprays for nasal administration, dry powder or aerosolized formulations for inhalation, and the like. It should be understood that the formulations and compositions that would be useful in the present invention are not limited to the particular formulations and compositions that are described herein.

Powdered and granular formulations of a pharmaceutical preparation of the invention may be prepared using known methods. Such formulations may be administered directly to a subject, used, for example, to form a material that is suitable to administration to a subject. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may be prepared, packaged, or sold in a formulation suitable for pulmonary administration via the buccal cavity. Such a formulation may comprise dry particles that comprise the active ingredient and have a diameter in the range from about 0.5 to about 7 nanometers, and in certain embodiments from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In certain embodiments, such powders comprise particles wherein at least 98% of the particles by weight have a diameter greater than 0.5 nanometers and at least 95% of the particles by number have a diameter less than 7 nanometers. In certain embodiments, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in certain embodiments having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration in certain embodiments have an average diameter in the range from about 0.1 to about 200 nanometers.

The pharmaceutical composition of the invention may be delivered using an inhalator such as those recited in U.S. Pat. No. 8,333,192 B2, which is incorporated herein by reference in its entirety.

In certain embodiments, the composition of the invention comprises a stable dry powder blend containing an active agent; lactose particles, comprising lactose $H_2O$, gelatin and starch maize; sodium starch glycolate; magnesium stearate; and talc silicified, comprising talc purified and colloidal silicon dioxide. In other embodiments, the dry powder comprises the active agent in an amount 4 to 0.02 mg per 100 mg of the dry powder. In yet other embodiments, the dry powder comprises lactose in an amount higher than 90 mg per 100 mg of the dry powder preparation. In yet other embodiments, the dry powder comprises lactose particles consisting of lactose $H_2O$, gelatin and starch maize, wherein the ratio by weight-mg of: "lactose $H_2O$":"gelatin":"starch maize" is 55-75:0.20-0.80:20-40. In yet other embodiments, the dry powder comprises sodium starch glycolate in an amount of 4-8 mg per 100 mg of dry powder. In yet other embodiments, the dry powder comprises magnesium stearate in an amount of 0.5-2 mg per 100 mg of dry powder. In yet other embodiments, the dry powder comprises talc silicified, in an amount of 2 mg per 100 mg of dry powder, wherein the talc silicified comprises talc purified and colloidal silicon dioxide in an amount of 0.667 mg of talc purified and 1.333 mg of colloidal silicon dioxide for 2 mg of talc silicified. In yet other embodiments, the blend further comprises a lake. In yet other embodiments, the dry powder comprises sodium starch glycolate in an amount of 5-6 mg per 100 mg of dry powder. In yet other embodiments, the dry powder comprises magnesium stearate in an amount of 1 mg per 100 mg of dry powder.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

Controlled Release Formulations and Drug Delivery Systems

In certain other embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds useful within the methods of the invention may be administered in the form of microparticles, for example by injection, or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 5 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain other embodiments, patients require intermittent treatment on a long-term basis upon any recurrence of symptoms and/or infection. In other embodiments, compounds are administered continuously throughout the lifespan of the subject, regardless of health or disease state.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 5 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Methods

Animal Procedure:

C57B1/6, 9-12 weeks-old, female mice were purchased from Taconic Lab. Mice were anesthetized by placing them in a chamber having paper towels soaked with 40% isoflurane solution. 1.5 U/kg of bleomycin (Hospira, Ill.) or equivalent volume (50 µl) of 0.9% normal saline was administered intratracheally. To test therapeutic efficacy in bleomycin-induced established fibrosis intraperitoneal thyroid hormone receptor beta agonist (GC-1, 30 µg/kg) was administered at days 10, 12, 14, 16 and 18 following bleomycin-administration and mice were sacrificed at day 21. The lungs were harvested for fibrotic assays Hydroxyproline: Lung hydroxyproline was analyzed with hydroxyproline colorimetric assay kit from Biovision (Milpitas, Calif.) following manufacturer's instruction.

qRT-PCR assay: Gene expression was determined by TaqMan® (Life Technologies, Thermo Scientific Inc. Rockford Ill., USA) according to manufacturer's instruction. β-glucuronidase (Gusb) was employed as an internal standard control and the specific primers and probes were all obtained from Life Technologies (Thermo Scientific Inc. Rockford Ill., USA). Each reaction was performed in triplicate. Relative gene expression was normalized to a value of 1.0 for the unstimulated control group.

Histology: Tissue sections (4 µm) were stained with Masson Trichrome (collagen/connective tissue), two slices per animal, and two animals per group.

Example 1

FIG. 1 illustrates an experiment where mice with bleomycin-induced fibrosis were treated with GC-1 intraperitoneally. On Day 0, bleomycin was delivered intratracheally to the mice (1.5 U/kg). On days 10-18, the mice were administered 30 µg/kg of GC-1 (200 µl) or equivalent volume of vehicle (normal saline 0.9%).

Figure 2A:
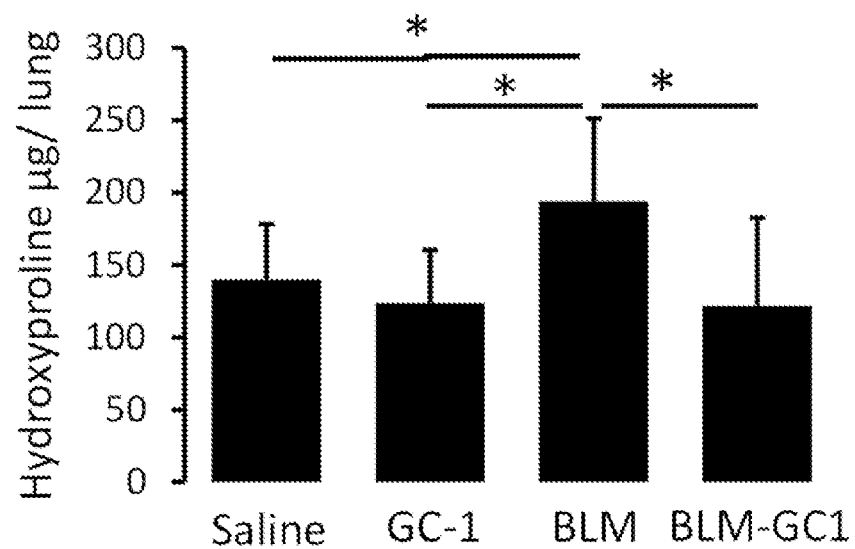
FIGS. 2A-2E illustrate the finding that GC-1 blunts established fibrosis in bleomycin induced lung fibrosis. 9-12 weeks-old, C57/BL6 female mice were treated every other day intraperitoneally with thyroid hormone agonist GC-1 (30 μg/kg) or equivalent volume of empty vehicle (200 μl of normal saline 0.9%) at days 10-18, following intratracheal challenge with bleomycin (1.5 U/kg) or normal saline 0.9%. Mice were sacrificed at day 21.
Figure 2B:
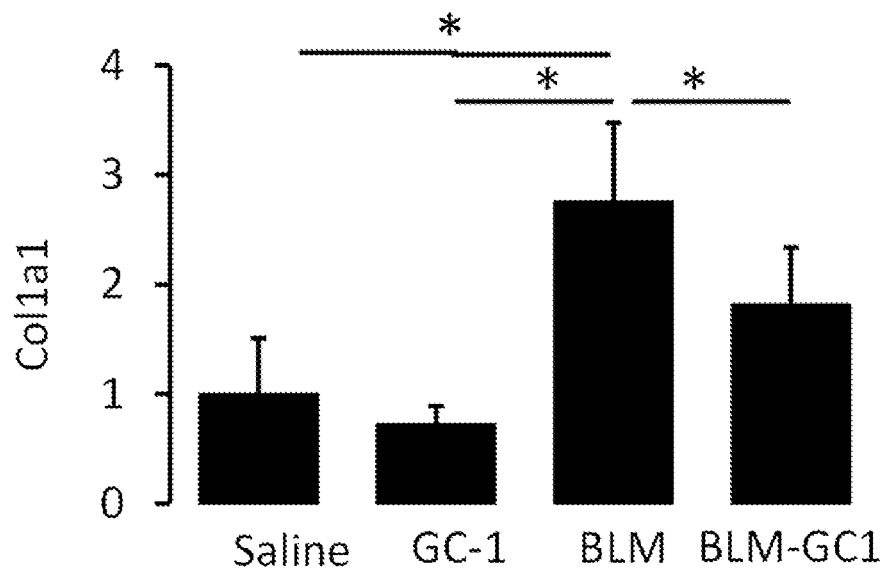
Figure 2C:
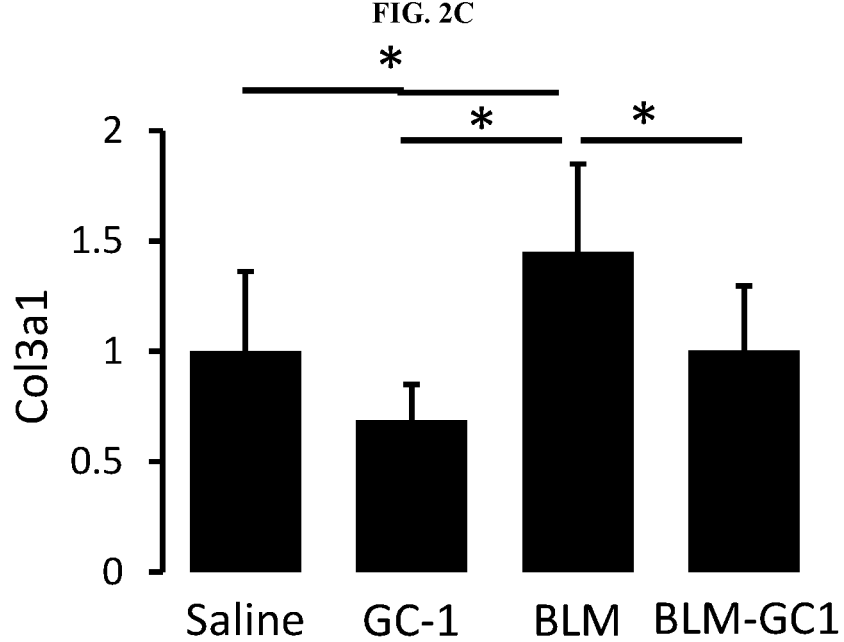
Figure 2D:
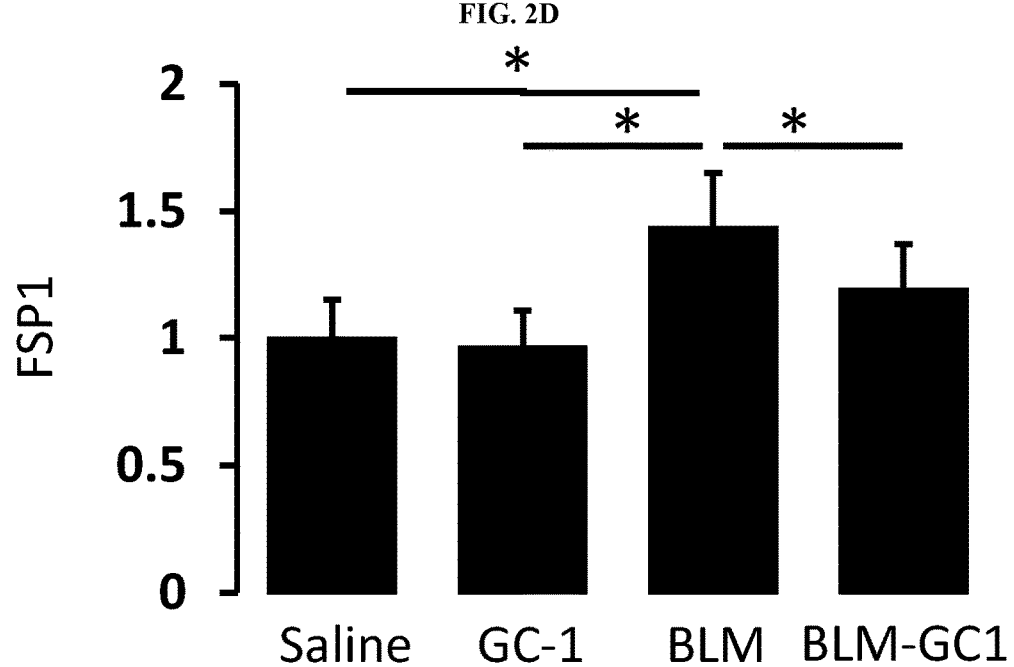
Figure 2E:
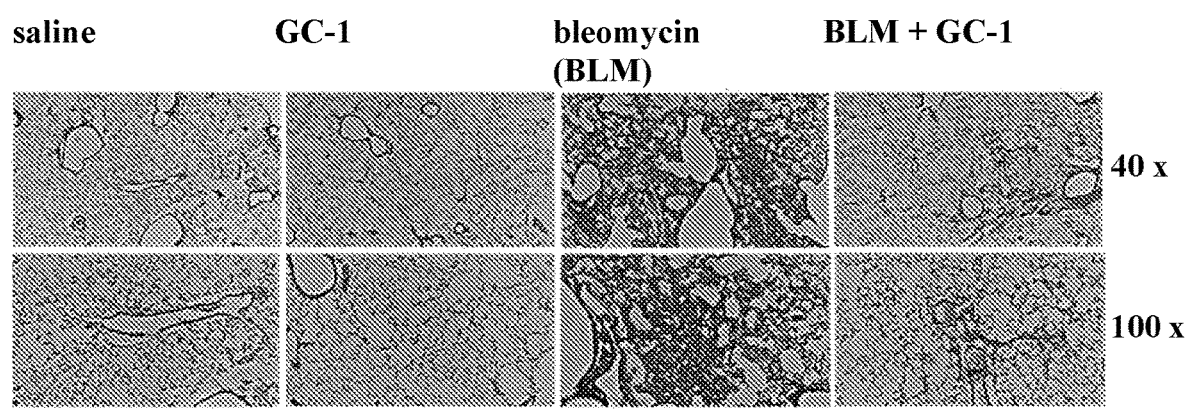

As illustrated in FIGS. 2A-2E, GC-1 was found to blunt established fibrosis in bleomycin induced lung fibrosis. 9-12 weeks-old, C57/BL6 female mice were treated every other day intraperitoneally with thyroid hormone agonist GC-1 (30 µg/kg) or equivalent volume of empty vehicle (200 µl of normal saline 0.9%) at days 10-18, following intratracheal challenge with bleomycin (1.5 U/kg) or normal saline 0.9%. Mice were sacrificed at day 21. As illustrated in FIG. 2A, collagen deposition in mice was assessed by hydroxyproline content. Data are expressed as mean hydroxyproline content per lung set (µg/gr lung)+SEM, n=8 mice/group, *p<0.05. FIGS. 2A-2D illustrate quantitative RT-PCR analysis of Col1a1, Col3a1, and FSP1 relative expression in the bleomycin model of lung fibrosis. Bars (means±SEM) are shown for the relative changes (fold) by setting the indicated control level to 1.0, *p<0.05. FIG. 2E illustrates Masson's Trichrome staining of representative lung sections (n=2) from each group of treated mice. A significant decrease in collagen deposition can be seen in the interstitium, peribronchiolar, or perivascular space in treated mice.

Figure 3A:
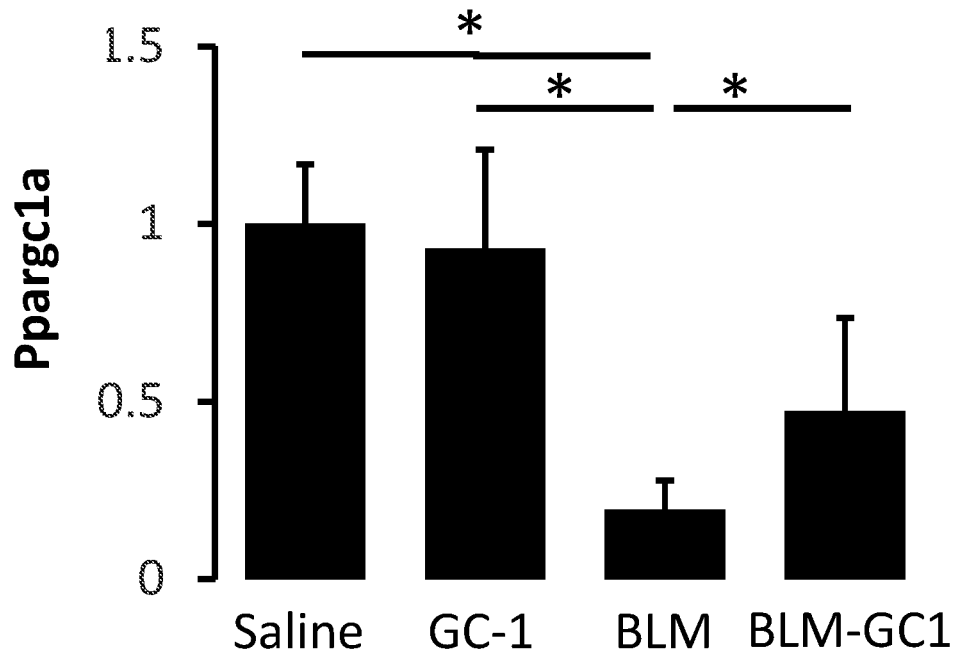
FIGS. 3A-3C illustrate the finding that GC-1 regulates expression of Ppargc1a (Peroxisome proliferator-activated receptor gamma coactivator 1-alpha), but not Thra (thyroid hormone receptor alpha) and Thrb (thyroid hormone receptor beta), in bleomycin induced mouse lungs. 9-12 weeks-old, C57/BL6 female mice were treated every other day intraperitoneally with thyroid hormone receptor beta agonist GC-1 (30 μg/kg) or equivalent volume of empty vehicle (200 μl of normal saline 0.9%) at days 10-18 following intratracheal challenge with bleomycin (1.5 U/kg) or normal saline 0.9%. Mice were sacrificed at day 21.
Figure 3B:
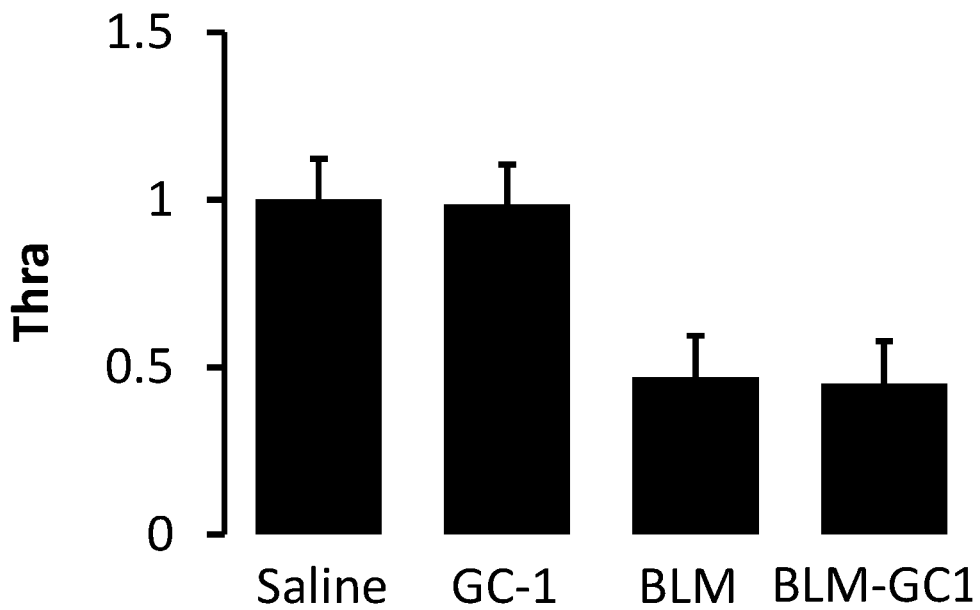
Figure 3C:
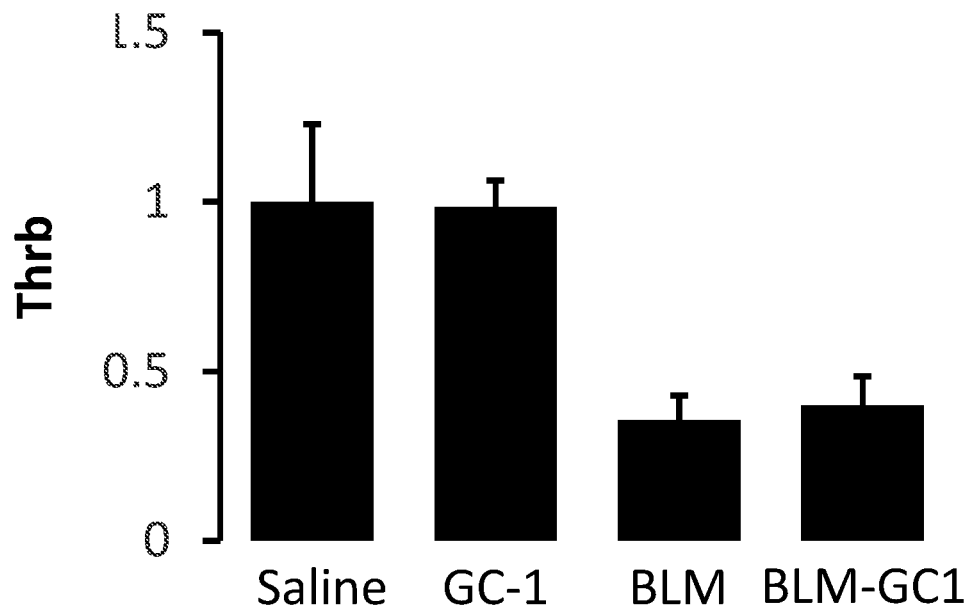

FIGS. 3A-3C illustrate the finding that GC-1 regulates expression of Ppargc1a, but not Thra and Thrb, in bleomycin induced mouse lungs. 9-12 weeks-old, C57/BL6 female mice were treated every other day intraperitoneally with thyroid hormone receptor beta agonist GC-1 (30 µg/kg) or equivalent volume of empty vehicle (200 µl of normal saline 0.9%) at days 10-18 following intratracheal challenge with bleomycin (1.5 U/kg) or normal saline 0.9%. Mice were sacrificed at day 21. FIGS. 3A-3C illustrate quantitative RT-PCR analysis of Ppargc1a, Thra and Thrb relative expression in the bleomycin model of lung fibrosis. Bars (means±SEM) are shown for the relative changes (fold) by setting the indicated control level to 1.0, n=8 mice/group, *p<0.05.

Example 2

Figure 4:
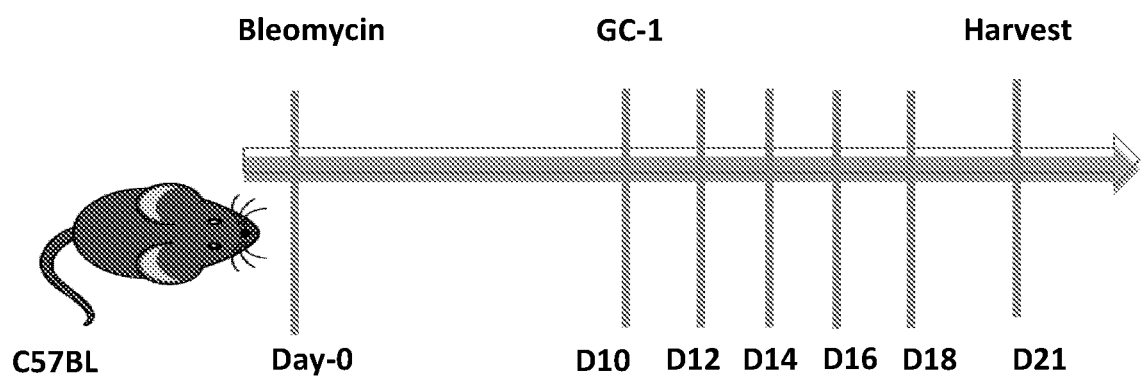
FIG. 4 illustrates a non-limiting experiment where mice with bleomycin-induced fibrosis were treated with GC-1 orally. On Day 0, bleomycin was delivered intratracheally to the mice (1.5 U/kg). On days 10-18, the mice were administered 5 mg/kg body weight of GC-1 (oral gavage) or equivalent volume of empty vehicle (200 μl of normal saline 0.9%).

FIG. 4 illustrates an experiment where mice with bleomycin-induced fibrosis were treated with GC-1 orally. On Day 0, bleomycin was delivered intratracheally to the mice (1.5 U/kg). On days 10-18, the mice were administered 5 mg/kg body weight of GC-1 (oral gavage) or equivalent volume of empty vehicle (200 µl of normal saline 0.9%).

Figure 5A:
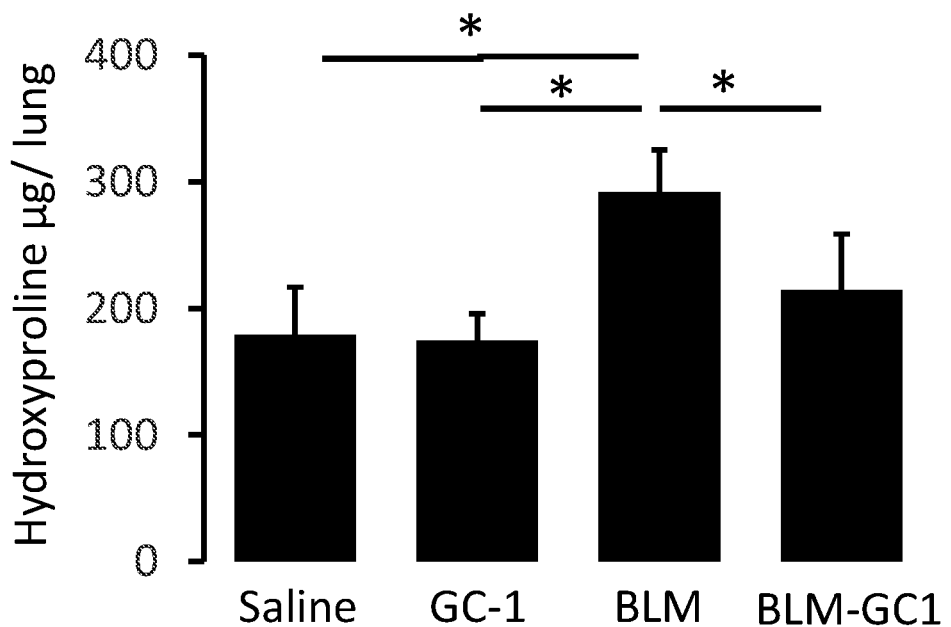
FIGS. 5A-5G illustrate the finding that GC-1 blunts established fibrosis in bleomycin induced lung fibrosis. 9-12 weeks-old, C57/BL6 female mice were treated every other day orally by gavage with thyroid hormone receptor agonist GC-1 (5 mg/kg) or equivalent volume of empty vehicle (200 μl of normal saline 0.9%) at days 10-18 following intratracheal challenge with bleomycin (1.5 U/kg) or normal saline 0.9%. Mice were sacrificed at day 21.
Figure 5B:
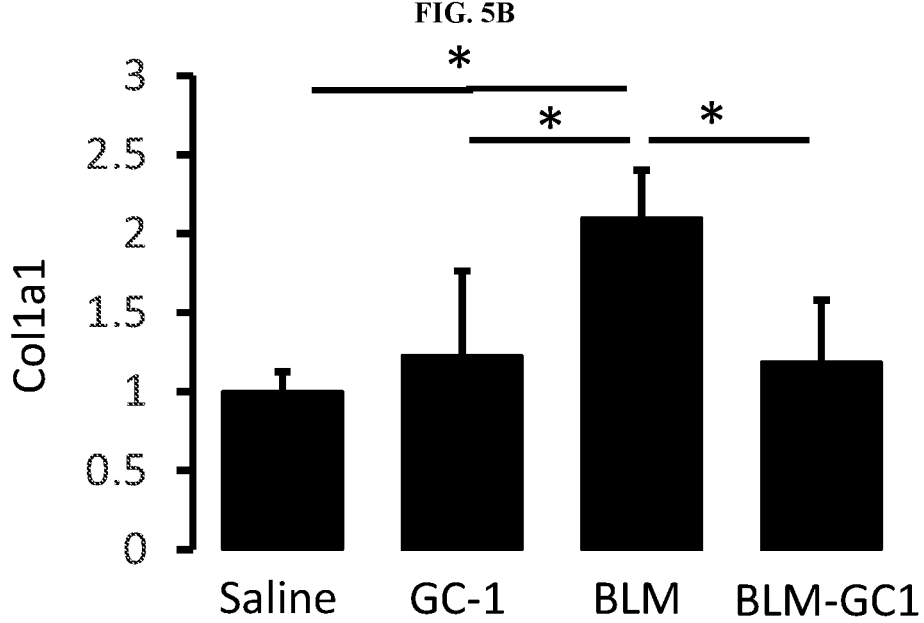
Figure 5C:
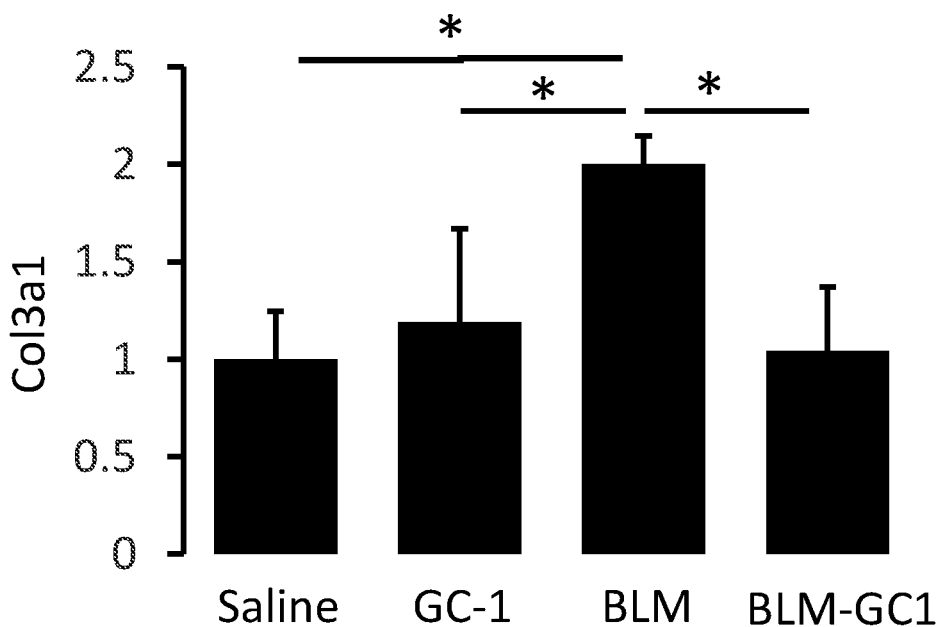
Figure 5D:
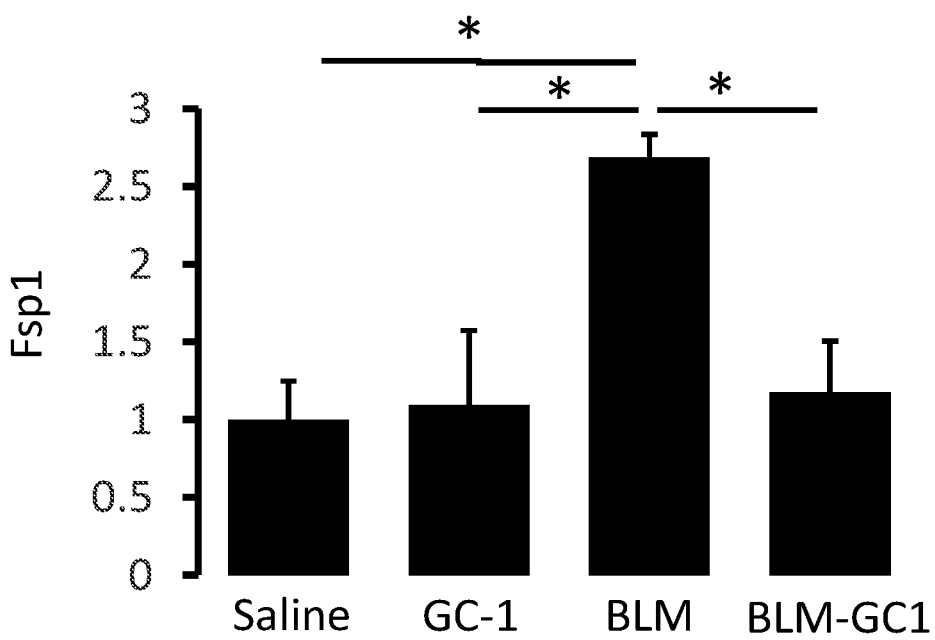
Figure 5E:
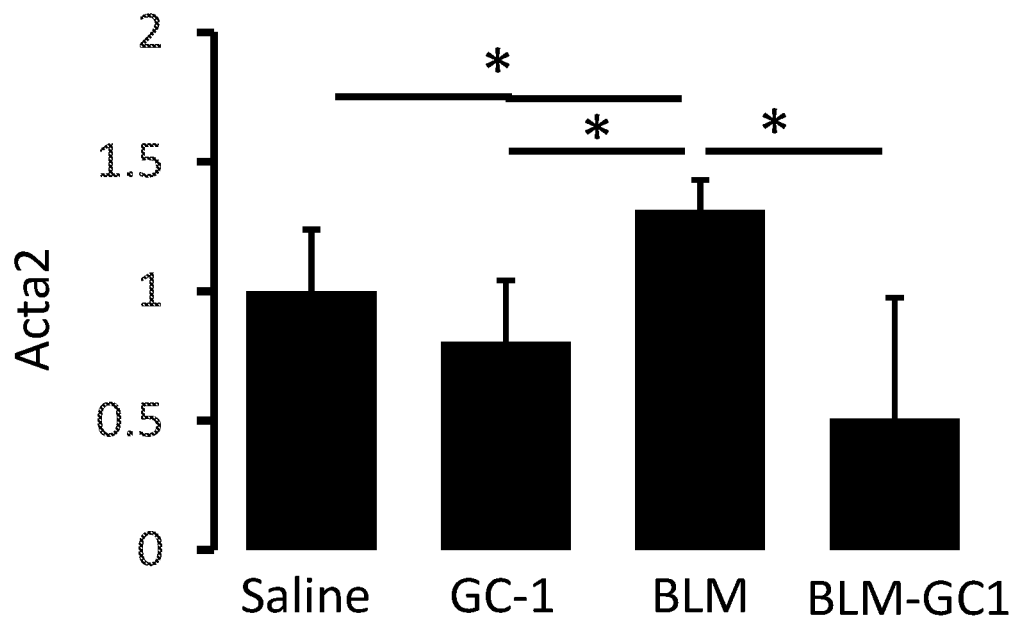
Figure 5F:
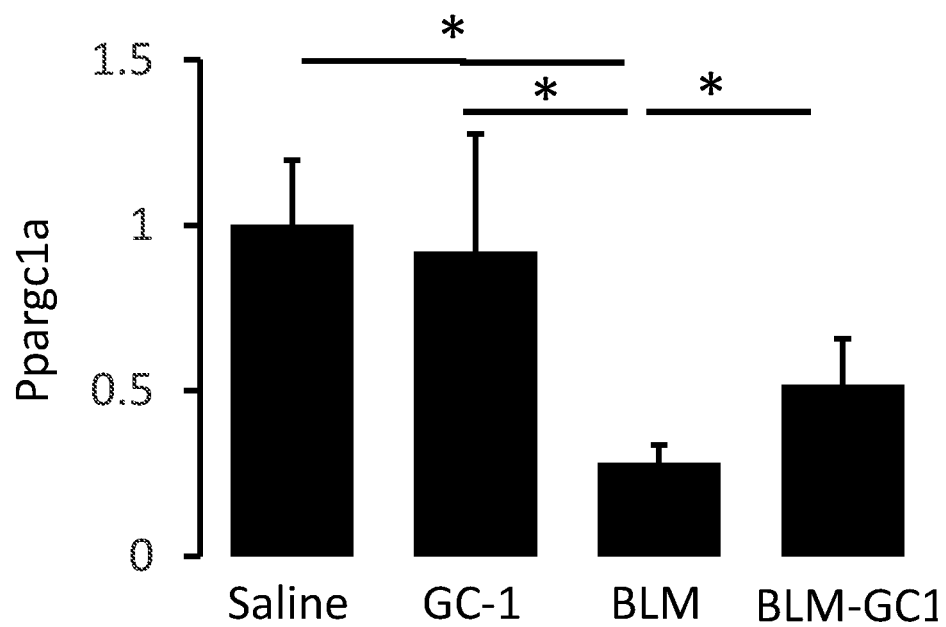
Figure 5G:
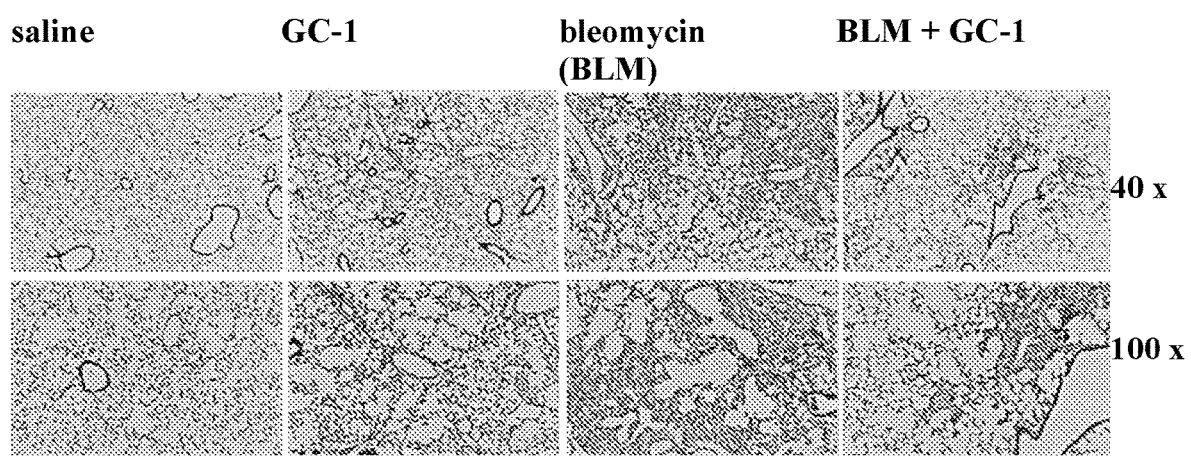

As illustrated in FIGS. 5A-5G, GC-1 was found to blunt established fibrosis in bleomycin induced lung fibrosis. 9-12 weeks-old, C57/BL6 female mice were treated every other day orally by gavage with thyroid hormone receptor agonist GC-1 (5 mg/kg) or equivalent volume of empty vehicle (200 µl of normal saline 0.9%) at days 10-18 following intratracheal challenge with bleomycin (1.5 U/kg) or normal saline 0.9%. Mice were sacrificed at day 21. FIG. 5A: Hydroxyproline level in mice was assessed. Data are expressed as mean hydroxyproline content per lung set (µg/gr lung)+SEM, n=8 mice/group, *p<0.05. FIGS. 5B-5F illustrate quantitative RT-PCR analysis of Col1a1 (collagen, type I, alpha 1), Col3a1 (collagen, type III, alpha 1), FSP1 (fibroblast-specific protein 1), Acta (alpha-actin-2), and Ppargc1a (peroxisome proliferator-activated receptor gamma coactivator 1-alpha) relative expression in the bleomycin model of lung fibrosis. Bars (means±SEM) are shown for the relative changes (fold) by setting the indicated control level to 1.0, *p<0.05. FIG. 5E illustrates Masson's Trichrome staining of representative lung sections (n=2) from each group of treated mice. A significant decrease in collagen deposition can be seen in the interstitium, peribronchiolar, or perivascular space in treated mice.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating or ameliorating a fibrotic lung disease in a subject in need thereof,
    the method comprising administering to the subject a therapeutically effective amount of GC-1 [2-(4-(4-hydroxy-3-isopropylbenzyl)-3,5-dimethylphenoxy) acetic acid], or any salt, ester, or solvate thereof.

2. The method of claim 1, wherein the fibrotic lung disease comprises idiopathic pulmonary fibrosis.

3. The method of claim 1, wherein the GC-1, or salt, ester, or solvate thereof, is the only pharmaceutically active agent administered to the subject.

4. The method of claim 1, wherein the GC-1, or salt, ester, or solvate thereof, is the only pharmaceutically active agent administered to the subject in sufficient amount to treat or ameliorate the fibrotic lung disease.

5. The method of claim 1, wherein the subject is further administered at least one additional agent that treats, ameliorates, or reduces the symptoms of the fibrotic lung disease.

6. The method of claim 5, wherein the at least one additional agent comprises at least one selected from the group consisting of pirfenidone and nintedanib.

7. The method of claim 1, wherein the subject is administered a dose of about 1 µg to about 10,000 mg of the GC-1, or salt, ester, or solvate thereof.

8. The method of claim 1, wherein administration of the GC-1, or salt, ester, or solvate thereof, does not cause significant or undesirable cardiac stimulation, weight loss, or blood lipid decrease in the subject.

9. The method of claim 1, wherein the GC-1, or salt, ester, or solvate thereof, is administered to the subject at a frequency selected from the group consisting of about three times a day, about twice a day, about once a day, about every other day, about every third day, about every fourth day, about every fifth day, about every sixth day, and about once a week.

10. The method of claim 1, wherein the GC-1, or salt, ester, or solvate thereof, is administered to the subject through a route selected from the group consisting of oral, parenteral, nasal, intravenous, subcutaneous, enteral, pulmonary, aerosol, ophthalmic, inhalational, intratracheal, intrabronchial, and topical.

11. The method of claim 1, wherein the subject is a mammal.

12. The method of claim 11, wherein the mammal is a human.

13. A method of treating or ameliorating idiopathic pulmonary fibrosis in a subject in need thereof, the method comprising administering to the subject a therapeutically effective amount of GC-1 [2-(4-(4-hydroxy-3-isopropylbenzyl)-3,5-dimethylphenoxy) acetic acid], or any salt, ester, or solvate thereof.

14. The method of claim 13, wherein the GC-1, or salt, ester, or solvate thereof, is the only pharmaceutically active agent administered to the subject.

15. The method of claim 13, wherein the GC-1, or salt, ester, or solvate thereof, is the only pharmaceutically active agent administered to the subject in sufficient amount to treat or ameliorate the idiopathic pulmonary fibrosis.

16. The method of claim 13, wherein the subject is further administered at least one additional agent that treats, ameliorates, or reduces the symptoms of the idiopathic pulmonary fibrosis.

17. The method of claim 13, wherein the subject is administered a dose of about 1 µg to about 10,000 mg of the GC-1, or salt, ester, or solvate thereof.

18. The method of claim 13, wherein administration of the GC-1, or salt, ester, or solvate thereof, does not cause significant or undesirable cardiac stimulation, weight loss, or blood lipid decrease in the subject.

19. The method of claim 13, wherein the GC-1, or salt, ester, or solvate thereof, is administered to the subject at a frequency selected from the group consisting of about three times a day, about twice a day, about once a day, about every other day, about every third day, about every fourth day, about every fifth day, about every sixth day, and about once a week.

20. The method of claim 13, wherein the GC-1, or salt, ester, or solvate thereof, is administered to the subject through a route selected from the group consisting of oral, parenteral, nasal, intravenous, subcutaneous, enteral, pulmonary, aerosol, ophthalmic, inhalational, intratracheal, intrabronchial, and topical.

21. The method of claim 13, wherein the subject is a mammal.

22. The method of claim 21, wherein the mammal is a human.

* * * * *